United States Patent [19]

Cook

[11] Patent Number: 5,364,341
[45] Date of Patent: Nov. 15, 1994

[54] IRRIGATION/ASPIRATION VALVE AND PROBE FOR LAPAROSCOPY

[75] Inventor: John D. Cook, Prior Lake, Minn.

[73] Assignee: Inlet Medical, Eden Prairie, Minn.

[21] Appl. No.: 64,827

[22] Filed: May 19, 1993

Related U.S. Application Data

[62] Division of Ser. No. 911,764, Jul. 10, 1992, Pat. No. 5,241,990.

[51] Int. Cl.$^5$ ............................................. A61M 1/00
[52] U.S. Cl. ...................................... 604/30; 604/34; 604/902
[58] Field of Search .................. 433/91, 92, 95; 137/845; 604/20, 30, 34, 167, 247, 905, 902

[56] References Cited

U.S. PATENT DOCUMENTS

| D. 271,421 | 11/1983 | Fetterman | 604/248 |
|---|---|---|---|
| 806,079 | 11/1905 | Gavelek | 251/209 |
| 2,902,253 | 9/1959 | Page | 251/209 |
| 3,012,752 | 12/1961 | Buck | 251/904 |
| 3,774,604 | 11/1973 | Danielson | 251/904 |
| 3,788,599 | 1/1974 | Cloyd | 251/904 |
| 3,834,372 | 9/1974 | Turney | 604/248 |
| 3,890,712 | 6/1975 | Lopez | 433/92 |
| 4,003,403 | 1/1977 | Nehring | 251/904 |
| 4,158,916 | 6/1979 | Adler | 433/91 |
| 4,227,533 | 10/1980 | Godfrey | 604/247 |
| 4,342,315 | 8/1982 | Jackson | 433/95 |
| 4,667,927 | 5/1987 | Oscarsson | 251/209 |
| 4,758,235 | 7/1988 | Tu | 604/248 |
| 4,973,319 | 11/1990 | Melsky | 604/247 |
| 5,019,054 | 5/1991 | Clement et al. | 604/32 |
| 5,074,334 | 12/1991 | Onodera | 604/32 |

FOREIGN PATENT DOCUMENTS

| 3503320 | 8/1986 | Germany . | |
| 727959 | 4/1955 | United Kingdom | 604/247 |
| 741551 | 12/1955 | United Kingdom | 433/91 |

OTHER PUBLICATIONS

Solos Endoscopy Product Literature (date unknown).
Accu-Beam Product Literature, TTI Medical (date unknown).
Apple Medical Product Literature (data unknown).

Primary Examiner—Jerome L. Kruter
Attorney, Agent, or Firm—Merchant, Gould, Smith, Edell, Welter & Schmidt

[57] ABSTRACT

The invention is a valving device for use in laparoscopic surgery. The device generally has a valve housing having a wall defining a common channel. The channel includes at least first and second apertures extending through the channel wall to allow fluid communication to and from the channel. The invention also includes a laparoscopic probe having a channel created by a wall defining a first open end and a second open end, as well as a valve for trapping debris positioned within the channel first open end.

19 Claims, 5 Drawing Sheets

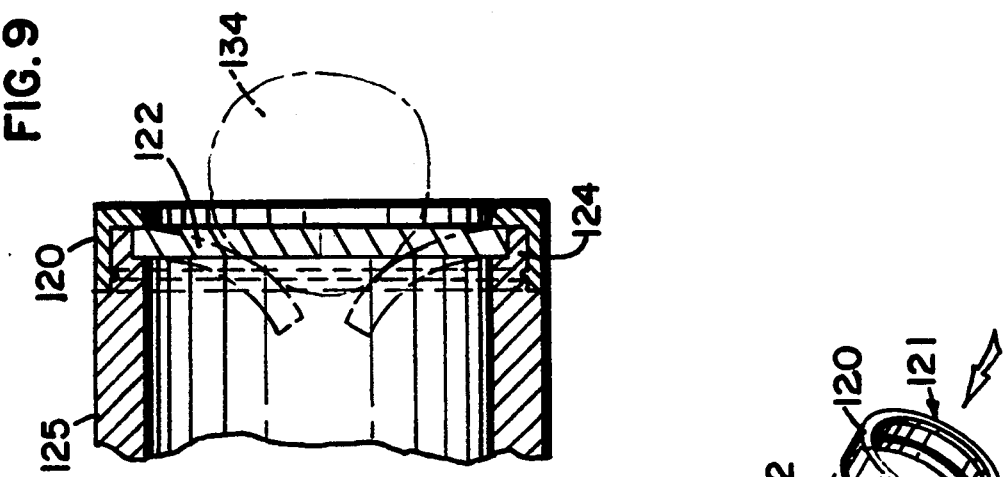
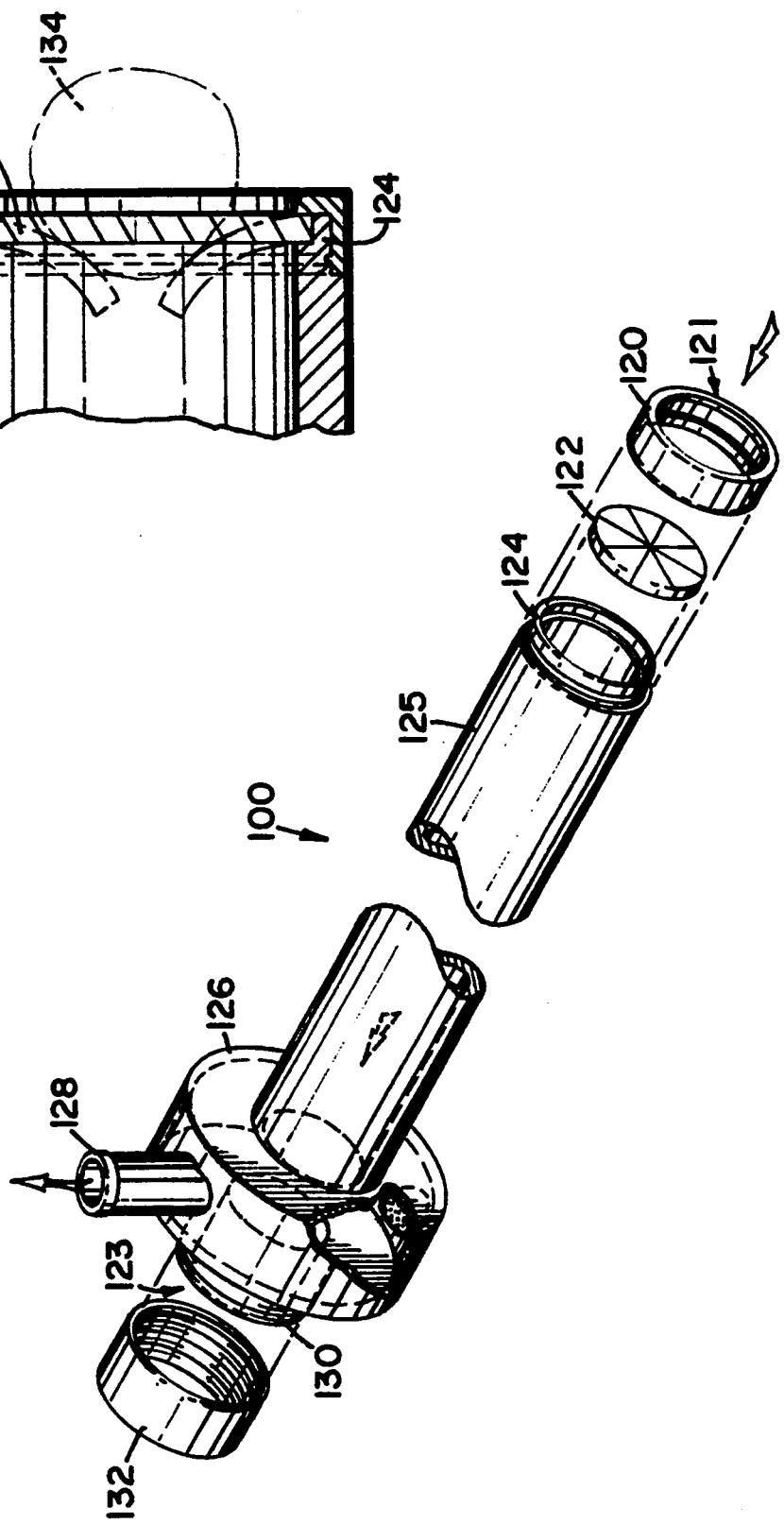

IRRIGATION/ASPIRATION VALVE AND PROBE FOR LAPAROSCOPY

This is a division, of application Ser. No. 911,764, filed Jul. 10, 1992 now U.S. Pat. No. 5,241,990.

FIELD OF THE INVENTION

This invention relates to an irrigation and aspiration valve for use in laparoscopy. This invention further relates to a probe arrangement for use in laparoscopy.

BACKGROUND OF THE INVENTION

Laparoscopy, or laparoscopic surgery, is a surgical procedure for gaining access to a patient's internal organs or tissue without making large incisions. Traditional surgical techniques required making a slit through a patient's skin, and frequently muscles and other tissue, to expose the organ or tissue to be operated.

Laparoscopy eliminates the need for large incisions, by providing access to the tissue or organ to be treated by making a number of relatively small holes through the patient's skin. These holes, typically having a diameter of between about 0.1 and 0.45 inch, may generally be located in, for example, a triangular arrangement in the vicinity of the tissue or organ to be operated on. Each of these holes serve multiple purposes. One of the holes may be used for inserting a tube through which gas is pumped, such as carbon dioxide to inflate the area around the organ or tissue to be operated on. In another of the holes, a camera or other device for transmitting a visual image of the surgical area, is inserted, such that the area undergoing surgery will be visible on a remote monitor.

In another of the holes, any one of a number of surgical instruments can be inserted. One of the instruments may be simply a probe or tube to allow fluid or debris to be passed therethrough, as will be described further below. Alternatively or additionally, the probe may have an integral or ancillary surgical instrument, such as a laser fiber, forceps, electrosurgical devices, or a cauterizing device. During the laparoscopic surgery, the surgeon manipulates the probe while watching the movement of the probe on the monitor.

Laparoscopic surgery gained its popularity in gynecological surgeries. The surgery is gaining popularity as it is being expanded to other specialists for diseases in other areas of the body, e.g. gall stones.

Because the laparoscopic patient does not have a large incision, the patient has a relatively short recovery time. A patient typically can return to nearly full activity within a matter of days. In contrast, the healing from a traditional type of incision can take considerably longer and be considerably more painful. Further, the danger of infection may be considerably reduced with laparoscopy.

The use of laparoscopic surgery is described in greater detail below through the example of the removal of a gall stone. It is to be understood, however, that the functions and operation of the laparoscopic equipment would be similar for a number of different types of surgical procedures.

To remove a gall stone, the laparoscopic procedure would begin with the making of four holes in a generally triangular pattern through the skin proximate the gall bladder. Into one of these holes, a tube would be inserted and carbon dioxide would be instilled therethrough to inflate the abdominal cavity. A camera or other detector for creating a visual image on a remote monitor would be inserted in the same or another of the holes, as described above. Probes and instruments would be inserted into the abdominal cavity. The surgeon would watch the surgical area on the monitor and manipulate the probe and instruments accordingly to appropriately treat the diseased organ. It is sometimes necessary to rinse or irrigate the area being operated on. This can be accomplished by providing fluid flow into the patient through a probe and thereafter vacuuming the fluid with the probe. The vacuum can also be used to remove blood, other fluids, smoke or debris from the surgical area. To accomplish this irrigation and aspiration, it is desirable that one or more valves be provided to control flow of fluids and particles into and out of the surgical area.

It is further desirable that a valve for controlling irrigation and aspiration be generally unitary and that both aspiration and irrigation be operable with one valve, or with one switch or handle, for convenience of the user. It is further desirable that the valve be constructed so that clogging of debris within the valve is minimized.

Still further, it is desirable for a valve arrangement in conjunction with the probe to be operable to allow a range of flow volumes for both irrigation and aspiration. This is desirable because, for example, as gas and fluid are pulled through the probe to the atmosphere outside of patient's body, additional $CO_2$ gas must be supplied to maintain relatively constant internal pressure. Typically the $CO_2$ gas, under pressure, is cooler than the patient's body temperature, and therefore the body cools somewhat as $CO_2$ gas is applied. It is preferable to maintain a relatively low flow rate of $CO_2$ gas to minimize the cooling of the patient's body. Therefore, slow or controlled withdrawal of fluids and gases from the body may be desirable to minimize the replacement volume of the $CO_2$ gas into the patient.

Existing probes typically have an outer shield tubing or sheath. In prior art probes, this shield is metallic or opaque. Because the probe sheath is not transparent, it is difficult for a surgeon or nurse to recognize from the image on the monitor when blood or fluid begins to be drawn into the probe until the blood is visible in the tubing outside the patient's body. Additionally, metallic tubes are undesirable because, when used with electrosurgical devices and cauterizing devices, capacitive coupling induces a current on the sheath tube, thereby causing it to burn tissue with which it comes into contact.

Thus, it would be desirable that a probe for use in laparoscopic surgery be made with a tube sheath of a clear material. With the use of clear material, the surgeon or nurse could immediately see that blood is passing into the probe tube. Further, a non-conductive material would not be subject to the build up of charge due to induced currents during electrosurgery and cauterizing, and therefore would not burn the tissue with which the probe comes into contact.

SUMMARY OF THE INVENTION

In light of the above-described problems with prior art devices, and in keeping with the objectives discussed above, the present invention provides a valving device and probe for use in connection with laparoscopic surgery. For purposes of the invention fluids comprise liquids, gases, and solid, semi-solid, or gelatinous debris contained within the liquid or gas as well as any other material evacuated from or flowed to, an operating field.

VALVING DEVICE

The device includes a valve housing which defines a common channel. The channel has at least one open end and includes two apertures directed through the side walls of the valve housing. A valve body is sized and shaped to be received within that common channel of the valve housing. The valve body is generally annular, and is .capped at one end and open at the opposite axial end. The annular wall of the valve body includes two apertures therethrough. By manipulation of the position of the valve body along a path, the apertures in the valve body and the valve housing can selectively be aligned to allow fluid flow to or from the inner flow chamber and the operating field. The probe channel, in use, is in fluid contact with the inner flow chamber within the valve body. Manipulation of the valve body allows selection of a desired flow rate, because the degree to which the apertures in the valve housing and of the valve body are aligned determines the size of the resulting aperture therethrough, and thereby determines the flow rate of fluid passing through the resulting aperture.

Because the valve body is generally annular, the ports, or the distance from the outside of the valve body to the inner flow channel, is relatively short. This arrangement discourages debris from lodging in the apertures. Further, because both ports are connected via a common flow channel, fluid passing through one of the channels assists in dislodging debris from the other aperture.

A detente or protrusion in the handle or actuation structure which controls the position of the valve body, cooperates with protrusions on the valve housing to provide preselected positions which correspond to predetermined volumetric flow rates.

PROBE

This invention further relates to a probe device having a clear sheath tube, such as polycarbonate, which is a clear, electrically and magnetically non-conductive material. Still further, the invention relates to a probe having a containment mechanism on its invasive end.

BRIEF DESCRIPTION OF THE DRAWINGS

In the drawings, in which like numerals are used throughout to identify corresponding elements through several views:

FIG. 8 is a side plan view of a laparoscopic probe in accordance with a further alternative embodiment of the invention.

FIG. 9 is a cross-sectional view of the probe as shown in FIG. 8 showing one embodiment of the containment means in accordance with this invention.

DETAILED DESCRIPTION OF THE PREFERRED EMBODIMENTS

Figure 1:
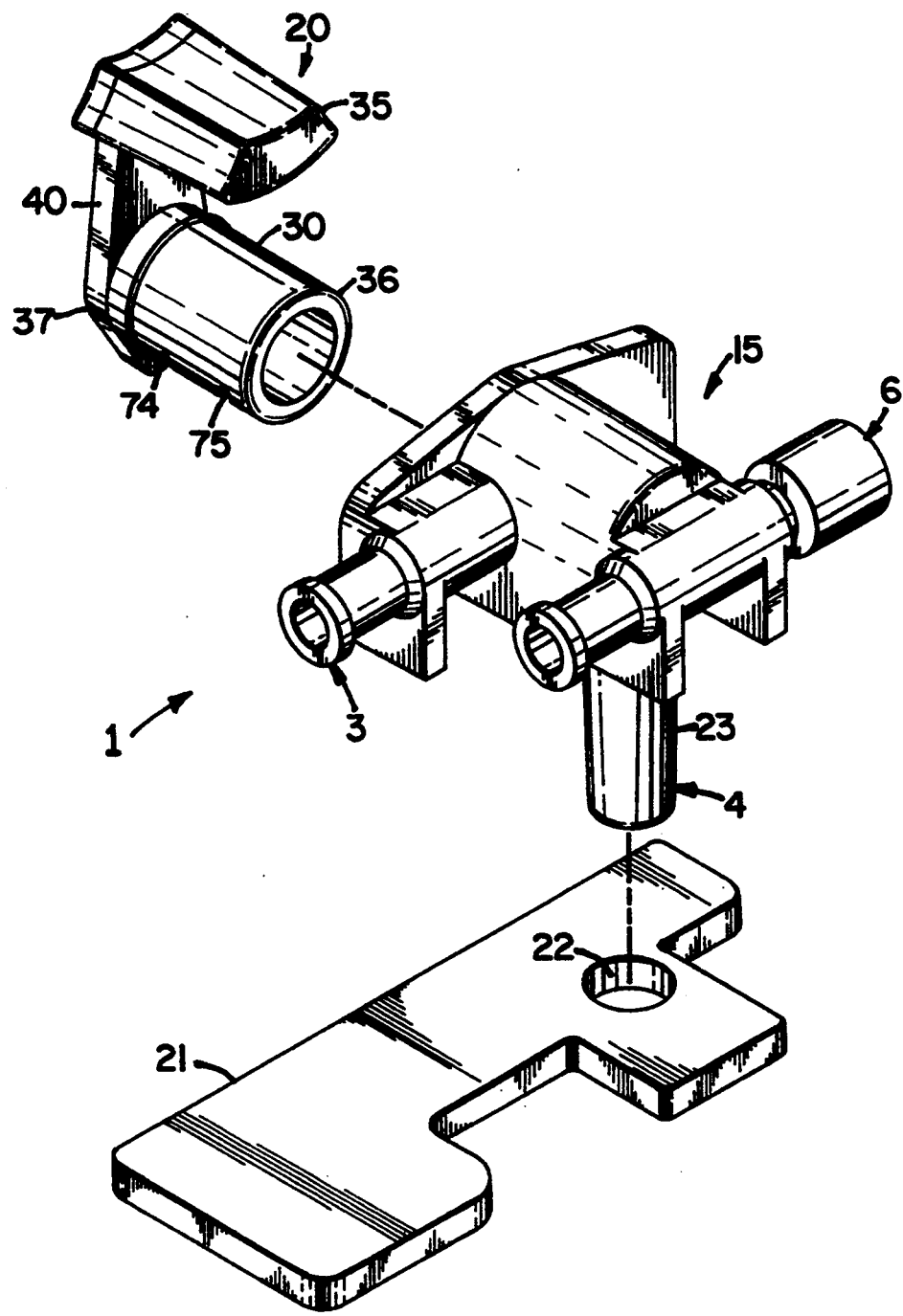
FIG. 1 is an exploded assembly view of a valve device according to the present arrangement.

A preferred embodiment of a valving device according to the present invention is illustrated in FIGS. 1–5. Generally, the valving device 1 includes an inlet port 3 and an outlet port 4. Additionally, the valving device 1 includes a port 6 for receiving a probe (probe not shown in FIGS. 1–3) therethrough. Inlet and outlet ports 3 and 4, respectively, can be perpendicular to one another in the illustrated embodiment. In typical use, the inlet port would be connected by fluid communication to a fluid supply source. Fluid to irrigate the surgical area would be instilled through the inlet port 3. In typical use, the outlet port 4 would be in communication to a vacuum source, and would suck or aspirate material and fluid from the surgical area.

Fluid communication between the surgical area and the atmosphere would be made via the probe that would be positioned on port 6 of the valving device 4. The cooperation of the inlet and outlet ports and the probe channel will be better understood from further discussion below. With continued reference to FIG. 1, it is illustrated that in a preferred embodiment of the valving device 1, the valving device includes a valve housing 15. In a preferred embodiment this valve housing 15 is formed of a unitary molded body.

The valving device 1 further includes a valve body 20 which is sized and shaped to be received within the valve housing 15, as illustrated by the assembly lines. An optional base 21 is provided to give the valving device a generally planer bottom surface for convenient use. An aperture 22 through the base 21 receives a tube 23 or the like extending from the outlet port 4 in the valve housing 15.

The preferred valve body has an annular valve wall or spool 30 and a thumb- or finger-operated handle 35. Annular valve wall 30 is open at one axial end 36 but closed or capped at the opposite axial end 37, such as by attachment to an extension 40 of handle 35.

Annular spool 30 is received within valve housing 15 as indicated by the assembly line. Spool 30 is rotatable about its longitudinal axis within valve housing 15, by moving handle 35 about that axis.

Figure 2:
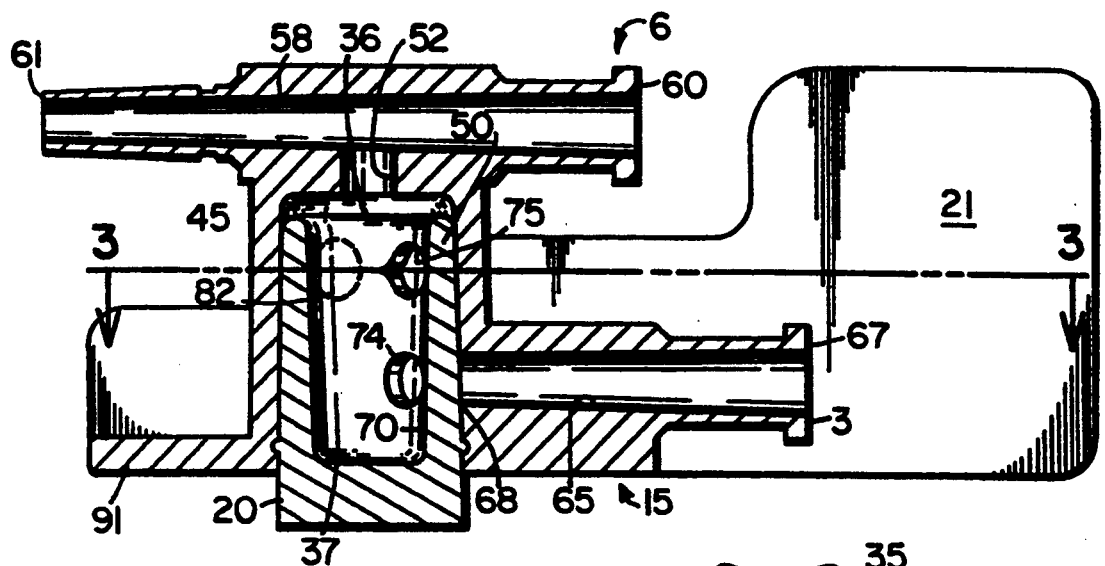
FIG. 2 is a cross-sectional view of the valving device illustrated in FIG. 1, taken from a top view.

Turning now to FIG. 2, it will be understood that portions of the valve housing 15 and the valve body 20 are illustrated in cross-section. In this view, vacuum or outlet port 4 is not visible. The hidden end of port 4 is indicated by the dotted line indicated at 45. As can be understood from FIG. 2, valve housing 15 defines a common channel 50. Common channel 50 is in fluid communication with the probe port 6 through connecting channel 52.

More specifically, one can see from FIG. 2 that port 6 includes a channel 58 therethrough defined by housing walls, into which a probe can be inserted. Port 6 has first inlet end 60, and a second outlet end 61. Port 3 similarly includes a channel 65 defined by the housing walls, and has an inlet end 67 and an outlet end 68.

FIG. 2 illustrates how the valve body 20 in the preferred embodiment is situated within the valve housing 15. As discussed above, valve body 20 is closed at one axial end 37 and open at the opposite axial end 36. In this way, the inner flow chamber 70 defined by annular wall 30 is in fluid communication with channel 58 of probe port 6 through connecting channel 52.

As illustrated, the preferred embodiment includes two apertures extending generally radially through the annular wall 30. These apertures are indicated at reference numbers 74 and 75. By selectively rotating valve body 20, apertures 74 and 75 are aligned with one of the inlet and outlet ports. For example, in an embodiment illustrated in FIG. 2, aperture 74 is positioned such that by rotation of valve body 20, aperture 74 becomes aligned with channel 65 with port 3. It will be understood that the resulting aperture between channel 65 and inner flow chamber 70 is determined by the amount of overlap between aperture 74 and the end 68 of port 3. Thus, by the positioning of valve body 20, the size of the resulting aperture between port 3 and flow chamber 70 can be adjusted between a very small size and a maximum size, generally equal to the size of aperture 74, or the size of inlet 68, whichever is smaller.

Figure 3:
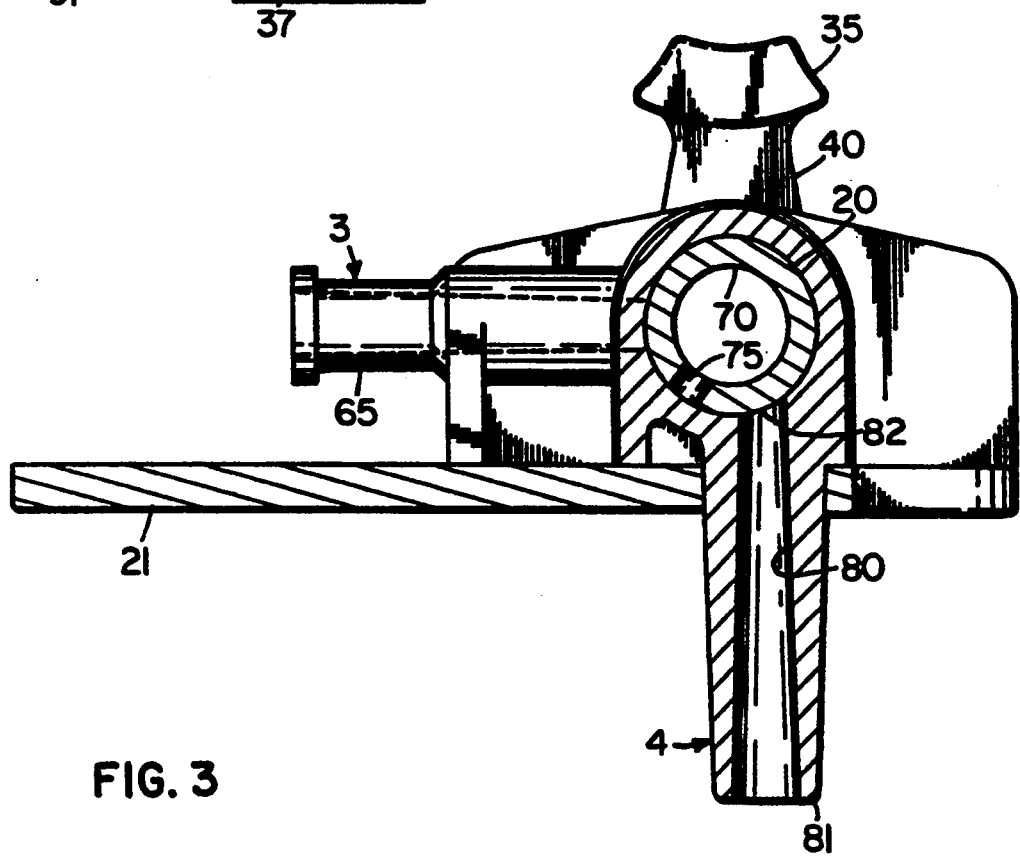
FIG. 3 is a side, cross-sectional view of the valving device illustrated in FIG. 1, with hidden portions illustrated in dotted lines.

Similarly, as will be understood with reference to FIG. 3, aperture 75 can be aligned, by rotating valve body 20, with channel 80 of port 4. Channel 80 has a first end 81 and a second opposite end 82. By rotating valve 20, aperture 75 will come into alignment with end 82 of channel 80. It will be understood that the resulting aperture between channel 80 and inner flow chamber 70 is determined by the amount of overlap between aperture 75 and end 82 of channel 80. Thus, by the positioning of valve body 20, the size of the resulting aperture between port 4 and flow chamber 70 can be adjusted between a very small size and a maximum size, generally equal to the size of aperture 75, or the size of end 82, whichever is smaller.

Thus, it will be understood that valve body 20 rotates, such that the apertures 74 and 75 travel in an arcuate path which brings them into alignment with respective channels 65 and 80. Because valve body 20 can be positioned at any point along the arcuate path, the resulting aperture between the respective channel and the inner flow chamber can be adjusted. Along a portion of the arcuate path, one or both of apertures 74 and 75 will not be aligned with respective channels 65 and 80 at all, in which case, the associated port 3 or 4 will be closed.

The apertures 74 and 75 as illustrated are generally circular. It is, however, to be understood, that the apertures may take on different shapes, such as tear-drop shaped (as can be seen in FIG. 2 at 75) to further enhance the ability to regulate the amount of flow between the respective port and the inner flow chamber. One aperture may be used to wash another aperture during any given procedure to facilitate removal of debris such as blood clots or tissue.

The valve body 20 may be calibrated, such that a particular rotational orientation of the valve body 20 within the valve housing 15 corresponds to particular flow rates through ports 3 or 4.

Figure 4:
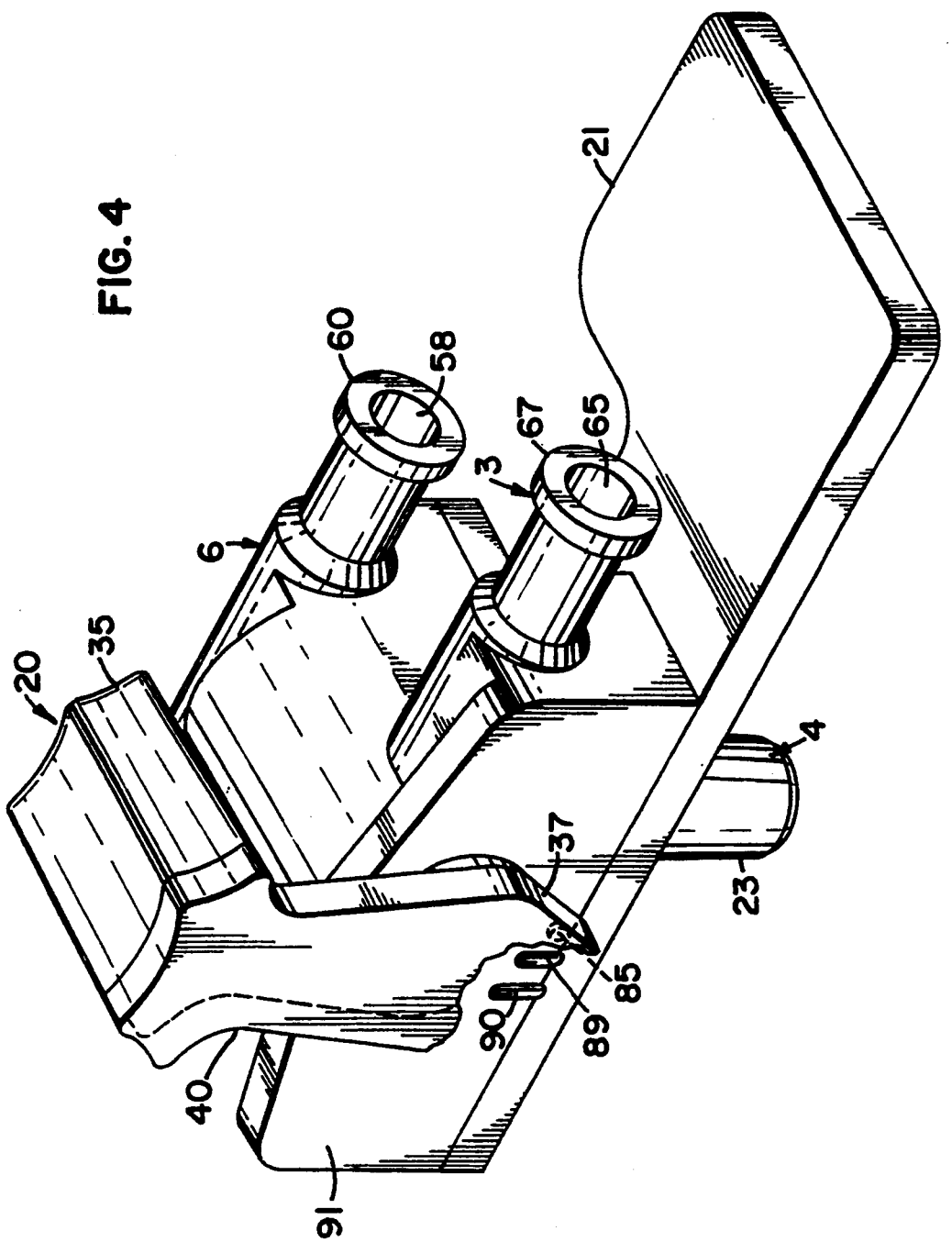
FIG. 4 is an elevated perspective view with portions cut away, of the valving device illustrated in FIG. 1, shown from a reversed angle.
Figure 5:
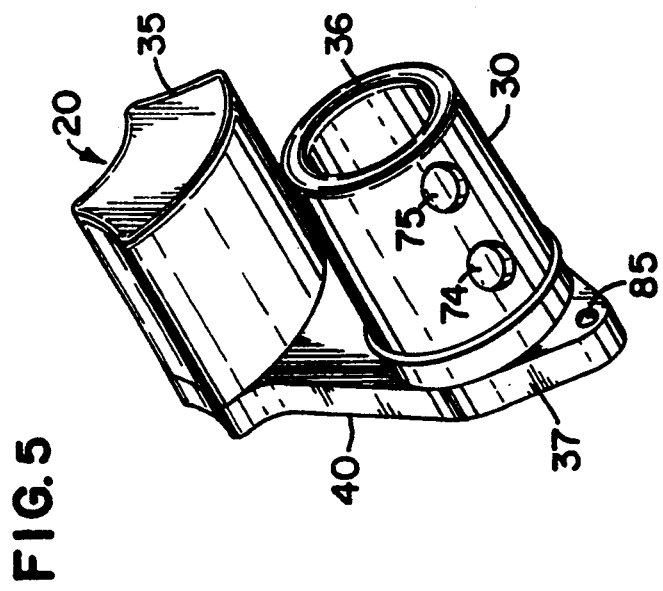
FIG. 5 is an elevated perspective view of a valve body, which is a portion of the valving device illustrated in FIG. 1.

As can be seen with reference to FIG. 5, a preferred valve body 20 includes a protrusion 85, proximate the bottom portion of extension 40. As illustrated in FIG. 4, the valve housing 15 has protrusions 89 and 90 extending outwardly from a wall 91 of the housing 15. Housing protrusions 89 and 90 are located to lie along the arcuate path that protrusion 85 travels as valve body 20 rotates within housing 15. In this way, protrusions 89 and 90 frictionally cooperate with or rub against protrusion 85 creating some resistance against the rotation of the valve body 20.

In this manner, the user can identify predetermined rotational orientations of the valve body which correspond to particular flow rates through ports 3 and 4. For example, by placing the valve body 20 in the forward position the outlet may be opened and by placing the valve body 20 in the rear position the inlet may be open. By placing the valve body 20 in the middle position both the inlet and outlet may be closed. It will be understood that the positioning of protrusions 85, 89, and 90 is related to the circumferential location of apertures 74 and 75 in the valve spool 30.

In typical use, to irrigate or supply fluid to a surgical area, valve body 20 is rotated such that at least a portion of aperture 74 is in line with a portion of outlet 68 of channel 65. For maximum flow, aperture 74 is centered on or co-axial with outlet 68. Water or other fluid is pumped through channel 65 through aperture 74, into inner flow chamber 70, through connecting channel 52, through probe channel 58, and into the surgical area.

To remove debris or fluid from the surgical area, valve body 20 is rotated to a position in which aperture 75 is at least partially in line with outlet 82 of channel 80. For maximum flow, aperture 75 is generally co-axial with end 82 of channel 80. Vacuum is applied to port 4 such that material from the surgical area flows through the probe, through channel 58, through connecting channel 52, into inner flow chamber 70, through aperture 75, and finally through channel 80 into a disposal container.

Annular wall 30 is preferably relatively thin. The distance across the valve that fluid or debris must pass is relatively small. Preferably, annular wall has a thickness of generally between 0.5 mm to 3 mm, and preferably about 1 mm and 2 mm. This minimizes the amount of debris that can become lodged in apertures 74 and 75. Further, since apertures 74 and 75 are in fluid communication, aperture 75 can be flushed by irrigation through port 3.

PROBE

In accordance with another aspect of the invention, there is provided a probe as seen in FIGS. 6–9 wherein like parts are designated with like numerals throughout several views.

The invention also comprises a laparoscopic probe including a transparent channel. The function of this transparent channel is to allow the physician or other medical personnel to ascertain the effectiveness of the laparoscopic surgical maneuver by viewing the flow of material through the probe. Often times the only manner to determine whether adequate irrigation flow or debris removal is taking place from the site of the operation is to look at the tubes used in conjunction with the laparoscopic valves and probes. The probe of the invention allows a physician or other medical personnel to determine material flow by looking directly at the transparent channel.

Generally, any organic or inorganic material which is transparent or translucent enough to allow medical personnel to visualize flow may be used in conjunction with the invention. Preferably, the material used for the transparent channel is inert or non-reactive to various bodily elements as well as being approved for medically invasive procedures.

Materials which may be useful include thermoplastic and thermosetting polymers including polymers of ethylene or propylene and the like, vinyl chloride, styrene, butadiene, urea, isocyanurate, carbonate, acrylics, epoxies, acetals, or mixtures thereof; secondary, ternary, or quaternary ceramics such as those made from boron, aluminum, iron, calcium, magnesium, oxygen, silicon, and mixtures thereof including and silicas and silica glasses, among others. One composition found preferable in accordance with the invention is polycarbonate such as that sold by Dow Corning under its Calibre 20980-10 designation. Generally, the diameter of the channel will range from about 3 to 12 millimeters and the length of the channel will range from about 28 to 42 centimeters. The outer shape of the probe is generally cylindrical but may be cubic, pentagonal, hexagonal, etc. as long as proper sealing means are provided.

A probe comprising a transparent channel may be used for any number of applications including the transport, attachment, or manipulation of any surgical devices useful in laparoscopic procedures such as electrosurgical knives, morselators, graspers, as well as for irrigation, aspiration, or entrapment.

Figure 6:
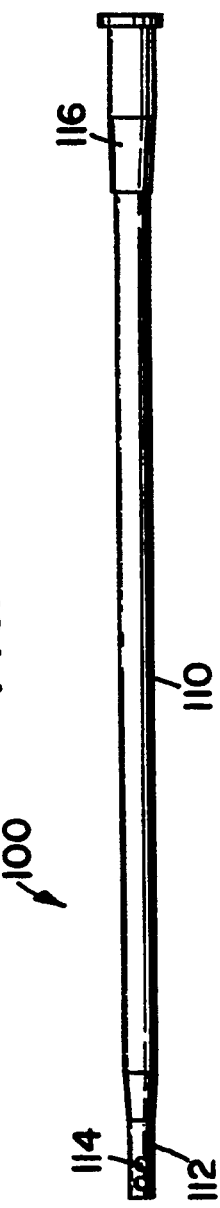
FIG. 6 is a side plan view of a laparoscopic probe in accordance with the invention.

One probe useful for laser transport may be seen in FIG. 6. Probe 100 comprises a transparent channel 110 which has at its first end a metal tip 112. The metal tip facilitates the action of the probe and prevents melt decomposition of the transparent channel 110. Additionally, the metal tip 112 may comprise sump holes 114 which facilitate the avoidance of tissue damage when the probe is used in aspiration or irrigation procedures. The sump holes avoid the incidence of too much pressure at the surface of tissue. Excess pressure may be vented through the sump holes 114. Fixture 116 at the second end of the probe is useful in affixing the probe to the valving mechanism disclosed in FIGS. 1–5.

Figure 7:
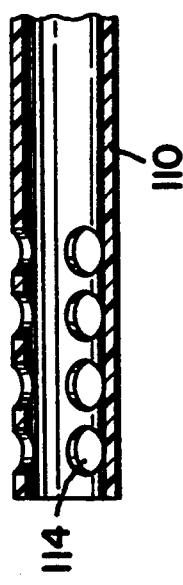
FIG. 7 is a partial side cut away view of a laparoscopic probe in accordance with the invention.

As can be seen in FIG. 7, sump holes 114 may also be placed directly in the transparent channel 110 of the probe. Further, sump holes 114 may be spaced and sized in a manner which would allow scaling or sizing of various objects or obstacles viewed through a monitor during the procedure. For example, the sump holes 114 may be sized at 1 millimeter to allow the physician or other medical personnel to calibrate the size of various objects within the operating field which appear on the monitor out of scale such as, for example, gall stone fragments. Additionally, as can be seen in FIG. 7, the regular placement of sump holes within a certain range of one another, such as 1 mm apart, allows the spacing to also be used as a means of scaling or sizing objects found within the operating field.

A further alternative aspect of the disclosed invention is a laparoscopic probe capable of capturing dislodged debris through aspiration while also allowing irrigation of an operating field. As can be seen in FIGS. 8 and 9, the probe 100 comprises a channel barrel 125 having a first end 121 and a second end 123. Positioned within the first end of the channel is a valve 122 which may be secured in place by a cap 120 fitted onto the first end 121 of said channel 100 through any number of means including threads, or frits 124. The probe may also comprise a containment or sump area 126 in which is held debris 134 such as calcium fragments and the like. At the second end 123 of the channel 100 a cap 132 may be positioned over this end through means 130 such as fritting or threading. Irrigation or aspiration may be effected through entry 128 affixed to sump means 126.

Generally, the probe 100 of the invention comprises a probe channel 125 which functions to deliver a specific physical or chemical effect to the operating field. Physical and chemical effects including procedures such as irrigation, cutting, removal, cauterization, aspiration, etc.

Generally, the probe channel 125 may comprise any material which is inert or non-reactive to the human anatomy. Further, the channel preferably comprises a material which is approved for invasive medical procedures. The material may comprise any organic or inorganic material commensurate with the functions detailed above which is transparent, translucent, or opaque, such as polymeric thermosetting and thermoplastic compositions; metals and metal alloys; or ceramic compositions such as silica or silica glasses.

Generally, the channel may comprise any variety of diameters, lengths or shapes commensurate in scope with the probe of FIGS. 6 and 7.

The disclosed probe 100 also comprises containment means such as a channel valve 122. Preferably, the valve functions to retain debris aspirated into the probe channel 125 while also allowing the passage of irrigating fluid through the channel without discharging the debris into the operating field. The valve may comprise any material which is patterned in accordance with this function which is inert and non-reactive to the environment within which it will be used, i.e., a human body cavity, and approved for invasive medical procedures. The channel valve 122 should also preferably comprise a material which is flexible enough to allow aspiration of debris into the probe channel 125 while also being capable of retaining entrapped debris within the probe channel 125 during irrigation procedures.

As can be seen in FIG. 9, operation of the probe during aspiration generally occurs by debris such as a calcium fragment 134 forcing the channel valve 122 to flex inwardly. Once in the probe channel 125, the debris may travel up the probe channel 125 by fluid pressure into the containment area 126 where it may be held in place by fluid pressure. In situations where a large volume of debris 134 is aspirated from the operating field, the entire probe channel 125 may be substantially filled without voiding of the probe. Further, the channel valve 122 may be positioned at any place throughout the length of the probe channel 125.

The probe 100 may then serve as a self-contained sample holder for use in, for example, pathological determination. To this end, the probe may be emptied through removal of cap 132 from the fritted or threaded 130 second end 123 of the probe 100.

Generally, the channel valve may comprise any material having suitable flexibility and resilience including synthetic or natural rubbery polymers such as rubbery block copolymers derived from monomers including styrene, acrylonitrile, butylene, isobutylene, isoprene, and others. Such polymeric and copolymeric compositions include butyl rubber, acrylonitrile-butadiene-styrene polymers, styrene-isoprene-styrene block copolymers, styrene-butadiene-styrene block copolymers, styrene-ethylene-butadiene-styrene block copolymers, and others.

Other flexible compositions which may be useful include polymers such as polyvinylchloride, polyalkylenes, polystyrenes, silicones including silicone rubber, polyester, polyetetrafluoroethylene, polyvinyl alcohol, polyacrylonitrile, polyacrylamide, cellulose and derivatives thereof, polysulfones, polyacrylates, polyvinyl pyrrolidones, and mixtures thereof including interpolymers, terpolymers, and as well as synthetic rubber derivatives such as silicone rubbers. Also useful are fluorocarbon based polymers and copolymers such as poly(vinylidene fluoride-co-hexafluoropropylene), poly(vinylidene fluoride-co-hexafluoropropylene-co-fluoroethylene, and poly(vinylidene fluoride-co-chlorotrifluoroethylene, among others; tetrafluoroethylene polymers such as polytetrafluoroethylene (PTFE), PTFE-hexafluoropropylene copolymers, PTFE-perfluorovinyl ether copolymers, and PTFE-ethylene copolymers among others.

One preferred class of compositions which have been found to be not only inert and non-reactive to the human anatomy but also readily acceptable for invasive medical use are silicone rubbers such as that sold by Dow Corning under the Silastic Q 7-4750.

The valve may be patterned in any fashion consistent with the function of this element of the invention. Specifically, the valve should be cut in a manner which allows for adequate transmission of debris 134 into the channel 125 without allowing the loss of the same debris 134 during a subsequent irrigation proceedings through the probe 100. To this end, the valve 122 may contain, for example, low diameter holes, slits of varying patterns, or any other means which will adequately allow the entrapment of debris.

One preferred pattern can be seen in FIG. 8 comprising a four-cut definition of the valve to create eight equally proportioned sections within the valve 122. Each of the cuts intersects across the center of the valve to create a "pie-shaped" configuration.

Generally, the thickness of the valve is determined by the relative needs of the application. To this end, we have found valve thicknesses to range generally from about 0.015 to 0.05 inch, preferably about 0.02 to 0.04 inch, and most preferably about 0.025 inch.

It is to be understood that even though numerous characteristics and advantages of a valving device and probe of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appendant claims are expressed.

I claim as my invention:

1. A laparoscopic probe comprising a channel, said channel comprising:
   (a) a wall defining first and second open ends;
   (b) a flexible valve for aspirating and entrapping debris drawn into said channel while allowing the passage of fluid out of the channel during irrigation, said valve positioned within said wall first open end, said valve comprising silicone rubber and having a thickness ranging from about 0.015 to 0.05 inches, wherein said valve is patterned to open inwardly allowing the aspiration and entrapment of debris, and valve patterning selected from the group consisting of low diameter holes, slits, and mixtures thereof;
   (c) a sump in fluid communication with said channel wall second open end, said sump comprising an outer wall defining a containment area, said sump outer wall having a greater diameter than said channel wall; and
   (d) a port, said port in fluid communication with said sump.

2. The probe of claim 1 wherein said wall comprises a transparent cylindrical tube.

3. The probe of claim 2 wherein said tube has a diameter ranging from 3 millimeters to 12 millimeters.

4. The probe of claim 1 wherein said valve comprises a flexible member.

5. The probe of claim 4 wherein said valve comprises silicone rubber.

6. The probe of claim 4 wherein said valve has one or more openings configured across the diameter of the valve.

7. The probe of claim 1 wherein said second open end comprise an outlet for the removal of debris.

8. The probe of claim 1 additionally comprising sump holes adjacent said probe wall first open end.

9. The probe of claim 8 wherein said probe wall comprises at least two sump holes calibratively positioned adjacent to each other.

10. The probe of claim 1 wherein said valve patterning comprises two or more slits running the diameter of the valve, wherein said slits intersect at the center of said valve.

11. A laparoscopic probe comprising channel means, said channel means comprising:
   (a) a wall defining first and second open ends; and
   (b) a flexible valve for aspirating and entrapping debris drawn into said channel while allowing the passage of fluid during irrigation, said valve positioned within said wall first open end, wherein said valve is patterned to open inwardly allowing the aspiration and entrapment of debris while also allowing the outward passage of irrigating fluid, said valve patterning selected from the group consisting of low diameter holes, slits, and mixtures thereof.

12. The probe of claim 11 wherein said valve comprises a composition selected from the group consisting of butyl rubber, an acrylonitrile-butadiene-styrene polymer, a styrene-isoprene-styrene block copolymer, a styrene-butadiene-styrene block copolymer, a styrene-ethylene-butadiene-styrene block copolymer, polyvinylchloride, a polyalkylene, a polystyrene, a silicone, a polyester, a polyetetrafluoroethylene, polyvinyl alcohol, polyacrylonitrile, polyacrylamide, cellulose, a cellulose derivative, a polysulfone, a polyacrylate, polyvinyl pyrrolidone, a poly(vinylidene fluoride-co-hexafluoropropylene), a poly(vinylidene fluoride-co-hexafluoropropylene-co-fluoroethylene, a poly(vinylidene fluoride-co-chlorotrifluoroethylene, a polytetra fluoroethylene, a PTFE-hexafluoropropylene copolymer, a PTFE-perfluorovinyl ether copolymer, a PTFE-ethylene copolymer, and mixtures thereof.

13. The probe of claim 11 wherein said valve comprises silicone rubber.

14. The probe of claim 11 wherein said valve has a thickness ranging from about 0.015 to 0.05 inches.

15. The probe of claim 11 wherein said valve patterning is selected from the group consisting of low diameter holes, slits, and mixtures thereof.

16. The probe of claim 11 wherein said valve patterning comprises two or more slits running the diameter of the valve, wherein said slits intersect at the center of said valve.

17. The probe of claim 11 wherein said probe channel comprises polycarbonate.

18. The probe of claim 11 wherein said probe channel has a diameter ranging from about 3 millimeters to about 12.

19. The probe of claim 11 wherein said probe comprises a steel tip at said channel first open end, said steel tip further comprising sump holes.

* * * * *